United States Patent [19]

Jay

[11] Patent Number: 5,536,645
[45] Date of Patent: Jul. 16, 1996

[54] NUTRITIVE MEDIUM FOR THE CULTURE OF MICROORGANISM

[75] Inventor: Corinne Jay, Villeurbanne, France

[73] Assignee: Bio Merieux, Marcy L'Etoile, France

[21] Appl. No.: 353,360

[22] Filed: Dec. 2, 1994

[30] Foreign Application Priority Data

Dec. 2, 1993 [FR] France .................................. 93 14687

[51] Int. Cl.$^6$ .............................. C12N 1/20; C12N 1/32; C12Q 1/18
[52] U.S. Cl. ........................ 435/32; 435/247; 435/253.6; 514/14; 514/15; 514/18
[58] Field of Search .................................... 514/2, 14, 15, 514/18; 435/32, 33, 240.3, 240.31, 247, 253.6, 256.8, 257.1, 258.1

[56] References Cited

U.S. PATENT DOCUMENTS

| | | | |
|---|---|---|---|
| 4,906,573 | 3/1990 | Barney et al. | 435/243 |
| 5,045,468 | 9/1991 | Darfler | 435/240.31 |

FOREIGN PATENT DOCUMENTS

| | | |
|---|---|---|
| 0019054 | 11/1980 | European Pat. Off. . |
| 0220379 | 5/1987 | European Pat. Off. . |
| 0283942 | 9/1988 | European Pat. Off. . |
| 60-098982 | 6/1985 | Japan . |

OTHER PUBLICATIONS

Database WPI, Section Ch, Week 8528, Derwent Publications, Ltd., London, GB; AN–85–168898 & JP–60 098982, Jun. 1, 1985—Abst.

M. J. Pelczar et al., "Synthetic Culture Media for Reference Use in Dairy Bacteriology", J. Milk Food Technology, vol. 14, 1951, pp. 90–91 and 97.

G. Gottschalk, Bacterial Metabolism, 2nd Edition, Chapter 1, pp. 1–4, 1988.

Methods for Dilution Antimicrobial Susceptibility Tests for Bacteria that Grow Aerobically, 2nd Edition, NCCLS Document M7–A2, vol. 10, No. 8, pp. Dec. 13, 1990.

M. Christe et al., "Susceptibilite du *Pseudomonas aeruginosa* aux aminosides: influence du calcium et du magnesium libres", Schweizerische Medizinische Wochenschrift, Journal Suisse de Médecine, 112, Nr. 7, 1982, pp. 234–241.

R. Then, "Mecanismes Moleculaires de la Bactericidie: Sulfamides et Trimethoprime", Bactericidie, pp. 89–91. 1990.

L. S. Klig et al., "Phospholipid Biosynthesis in *Candida albicans:* Regulation by the Precursors Inositol and Choline", Journal of Bacteriology, Aug. 1990, pp. 4407–4414.

B. M. Guirard et al., "Biochemical Factors in Growth," Manual of Methods for General Bacteriology, 1981, Chapter 7, pp. 79–82.

A. C. Gretler et al., "Vitamin Nutrition of the Staphylococci with Special Reference to Their Biotin Requirements," J. Bact., Dec. 1954, p. 44–49.

C. W. Tabor, "Polyamines in Microorganisms," Microbiological Reviews, Mar., 1985 pp. 81–99.

R. Y. Stanier et al., "The Aerobic Pseudomonads: a Taxonomic Study," J. gen Microbiol., vol. 43, No. 1, May 1966, pp. 159–181.

F. C. Neidhardt et al., Physiology of the Bacterial Cell A Molecular Approach, Chapter 3, pp. 97–98. 1990.

(List continued on next page.)

Primary Examiner—Jeffrey E. Russel
Attorney, Agent, or Firm—Oliff & Berridge

[57] ABSTRACT

The invention relates to a nutritive medium for the culture of microorganisms, containing alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, biotin, calcium pantothenate, folic acid, inositol, nicotinamide, vitamin B6, thiamine chloride, lipoic acid, choline, ethyl oxaloacetate, spermidine, Tween 80, purine and pyrimidine nucleosides, glucose, malic acid, iron, potassium, magnesium, calcium, sodium, chloride, phosphate ion, ammonium ion, acidic buffer, and basic buffer. The invention also relates to the use of such a medium.

13 Claims, 7 Drawing Sheets

OTHER PUBLICATIONS

M. J. Hall, "Roche Susceptibility Test (RST) medium, a defined formulation of susceptibility testing," Journal of Microbiological Methods, vol. 2, 1984, pp. 215–219.

P. D. Hoeprich et al., "Synthetic Medium for Susceptibility Testing," Antimicrobial Agents and Chemotherapy, 1970, pp. 494–497.

J. P. Flandrois et al., "Theories de Fonctionnement des Automates Pour Antibiogramme," l'antibiogramme automatise, pp. 17–22, 30. (1988).

R. D. Klein et al., "Short Communication Simplified Media for the Growth of Haemophilus influenzae from Clinical and Normal Flora Source," Journal of General Microbiology, vol. 113, 1979, pp. 409–411.

R. M. Lawrence et al., "Totally Synthetic Medium for Susceptibility Testing," Antimicrobial Agents and Chemotherapy, Mar. 1978, pp. 394–398.

P. F. Dougherty et al., "Chemically Defined Medium for Susceptibility Testing of Antimicrobial Agents," Antimicrobial Agents and Chemotherapy, Dec. 1976, pp. 923–925.

F. C. Neidhardt, *Escherichia coli* and *Salmonella typhimurium*, American Society of Microbiology, Washington, D.C., vol. 1, pp. 3–6. 1988.

F. C. Neidhardt et al., "Culture Medium for Enterobacteria," Journal of Bacteriology, Sep. 1974, pp. 736–747.

Manolo Gouy, "Origine et Fonction de l'utilisation de la degenerescence du code genetique chez *Escherichia coli*: Structuration en banque de donnees et analyse statistique des sequences nucleotidiques," Lyon, 1987, pp. 14, 29.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear     ( i i ) MOLECULE TYPE: peptide     ( x i ) SEQUENCE DESCRIPTION: SEQ ID NO:1:

Ala  Gly  Ser  Glu
    1

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear     ( i i ) MOLECULE TYPE: peptide     ( x i ) SEQUENCE DESCRIPTION: SEQ ID NO:2:

Glu  Asp  Arg  Pro  Pro  Leu  Phe  Gly  Gln  Gly  Thr  Val
    1                    5                          10

( 2 ) INFORMATION FOR SEQ ID NO:3:

( i ) SEQUENCE CHARACTERISTICS:
    ( A ) LENGTH: 11 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:3:

```
Ala  Ser  Asp  Ala  Lys  Ala  Tyr  Asp  Thr  Glu  Val
 1              5                        10
```

NUTRITIVE MEDIUM FOR THE CULTURE OF MICROORGANISM

The present invention relates to an essentially synthetic nutritive medium for microorganisms. In particular, the invention relates to a nutritive medium for the culture of microorganisms and its use in the determination of the activity of a substance active against the said microorganisms.

Essentially synthetic medium according to the invention is understood as meaning a medium of which at least the constituents indispensable for the obtainment of this medium having the properties described below are synthetic.

The qualities required of nutritive media for microorganisms are those described by Ericsson H. M. et al. (J. C. 1977, Antibiotic Sensitivity Testing, Report of an international collaborative study, Munksgaard, Copenhagen), namely:

- to allow the growth of the majority of clinically important bacteria without the necessity for further enrichment,
- to contain base elements (peptones) of satisfactory quality,
- to ensure reproducibility of the sensitivity tests whatever the batch and/or the supplier,
- not to show antagonism towards antibiotics,
- not to be subject to large pH variations,
- to be isotonic for bacteria and to withstand the addition of blood without provoking hemolysis.

The medium at present considered as reference medium by all specialists is Mueller-Hinton agar medium which satisfies comparatively well all these requirements. However, different problems are encountered which are a consequence of its complex character, Mueller-Hinton medium being made up of beef broth, casein hydrolysate and starch. Especially, as far as the study of antibiotics is concerned, a complex medium does not allow the concentration of the known constituents to be controlled, such as bivalent ions, thymidine, PBA (paraaminobenzoic acid) and folic acid, to optimize their activity, which makes tedious, or even impossible, any attempt aiming to correlate a difference in activity of an antibiotic with a difference in composition. Moreover, the composition of the Mueller-Hinton medium can vary not only from one batch to another in the production of the same supplier, but a large difference has been demonstrated on changing supplier. This variability in composition causes a lack of reproducibility of bacterial growth and of the activity of antibiotics. These problems are found to be increased with the liquid form of this medium, which additionally is not perfectly suited for use in an automated system, because of its mediocre optical qualities, owing to the fact that it contains sparingly soluble constituents such as starch.

To solve the reproducibility problems, media which are called synthetic have been proposed, that is to say media which are essentially devoid of natural components. Moreover, these media, when they are in liquid form, show an optical quality sufficient to allow reliable and reproducible measurements in automated systems.

However, generally speaking, the synthetic media described for the antibiogram are shown only for some species, often those having the lowest nutritive requirements, and their nutritive qualities are inferior to those of the reference Mueller-Hinton medium (see, for example, the articles of Hoeprich P. D. et al., Synthetic medium for susceptibility testing, Antimicrobial agents and chemotherapy (1970); Dougherty P. F. et al., Chemically defined medium for susceptibility testing of antimicrobial agents, Antimicrobial agents and chemotherapy, 10 (6) 2, 923–925 (1976), Lawrence R. M. et al., Totally synthetic medium for susceptibility testing, Antimicrobial agents and chemotherapy, Vol. 13, 3, 394–398 (1978)). Moreover, the Patent EP-0 019 054 describes a synthetic medium for the growth of microorganisms and its use for the determination of the activity of a substance therapeutically active against a microorganism. The composition of this medium means that it is only applicable to the growth and to the determination of the sensitivity to antibiotics of the more common germs and of anaerobic bacteria. Additionally, the determination of the sensitivity to antibiotics can only be carried out after incubation for 12 to 24 hours.

It therefore became necessary to have a synthetic medium which shows the nutritive qualities of the reference Mueller-Hinton medium and which, additionally, is suited for the growth and the determination of the sensitivity to antibiotics of bacteria most commonly clinically isolated.

In addition, the Applicant has developed a medium which meets the abovementioned requirements and which moreover, when it is in liquid form, allows a very rapid reading of the antibiogram, that is to say after 3 to 5 hours of incubation for enterobacteria and less than 10 hours for Pseudomonas by analysis of growth kinetics.

The medium according to the invention comprises a nutritive medium for the culture of microorganisms, characterized in that it contains 7–70 mg/l of alanine, 8–80 mg/l of arginine, 5–50 mg/l of asparagine, 6–60 mg/l of aspartic acid, 2–20 mg/l of cysteine, 4–40 mg/l of glutamine, 8–80 mg/l of glutamic acid, 7–70 mg/l of glycine, 2.5–25 mg/l of histidine, 6–60 mg/l of isoleucine, 9–90 mg/l of leucine, 9–90 mg/l of lysine, 4–40 mg/l of methionine, 5–50 mg/l of phenylalanine, 4–40 mg/l of proline, 4–400 mg/l of serine, 5–50 mg/l of threonine, 2–20 mg/l of tryptophan, 4–40 mg/l of tyrosine, 8–80 mg/l of valine, 0.01–0.2 mg/l of biotin, 0.01–0.3 mg/l of calcium pantothenate, 0.001–0.01 mg/l of folic acid, 0.01–0.5 mg/l of inositol, 0.04–0.2 mg/l of nicotinamide, 0.02–0.3 mg/l of vitamin B6, 0.01–0.1 mg/l of thiamine chloride, 0.005–0.05 mg/l of lipoic acid, 0.1–5 mg/l of choline, 1–10 mg/l of ethyl oxaloacetate, 0.1–1 mg/l of spermidine, 5–50 mg/l of Tween 80 [poly(oxy-1,2-ethanediyl) sorbitan mono-9-octadecenoate referenced under the number 7455 in THE MERCK INDEX (10th Edition)], purine and pyrimidine nucleosides in a ratio of the first to the second of between 1.5 and 2, purine nucleosides consisting of adenosine and guanosine, in a ratio of the first to the second of between approximately 0.8 and 1.2, pyrimidine nucleosides consisting of cytidine and uridine, in a ratio of the first to the second of between 1 and 3, 100–10,000 mg/l of glucose, 100–10,000 mg/l of malic acid, 0.02–0.583 mg/l of iron, 49.3–493 mg/l of potassium, 1.2–12 mg/l of magnesium, 2.7–27.2 mg/l of calcium, 1.18–3.15 g/l of sodium, 1,820–5,000 mg/l of chloride, 17.8–178.3 mg/l of phosphate ion, 33.6–336.0 mg/l of ammonium ion, 2,000–20,000 mg/l of an acidic buffer and 1,000–10,000 mg/l of a basic buffer.

In particular, the medium according to the invention contains 5–50 mg/l of adenosine, 3–30 mg/l of cytidine, 6–60 mg/l of guanosine, 1–10 mg/l of uridine, 0.2–5 mg/l of ferric pyrophosphate, 100–1,000 mg/l of dibasic potassium phosphate, 10–110 mg/l of magnesium chloride, 10–100 mg/l of calcium chloride, 100–1,000 mg/l of ammonium chloride and 3,000–8,000 mg/l of sodium chloride.

Advantageously, the medium of the invention moreover contains up to 0.022 mg/l of molybdenum, preferably in the form of ammonium molybdate, of concentration at most equal to 0.04 mg/l, up to 0.010 mg/l of cobalt, preferably in the form of cobalt chloride, of concentration at most equal to 0.04 mg/l, up to 0.027 mg/l of manganese, preferably in the form of manganese chloride, of concentration at most equal to 0.1 mg/l, up to 0.007 mg/l of zinc, preferably in the form of zinc sulfate, of concentration at most equal to 0.03 mg/l, up to 0.128 mg/l of copper, preferably in the form of copper sulfate, of concentration at most equal to 0.5 mg/l, up to 0.088 mg/l of boron, preferably in the form of boric acid, of concentration at most equal to 0.5 mg/l, up to 18.4 mg/l of sulfate ion, preferably in the form of potassium sulfate, of concentration at most equal to 100 mg/l, up to 0.1 mg/l of riboflavin, up to 0.005 mg/l of cyanocobalamin, up to 0.1 mg/l of menadione, up to 0.5 mg/l of boric acid and/or up to 5 mg/l of glycerol.

In the present invention, "up to" means to a concentration at most equal to.

Even more advantageously, the medium according to the invention contains 0.0005–0.005 mg/l of cyanocobalamin, 0.01–0.1 mg/l of menadione, 0.01–0.5 mg/l of mesoinositol, 0.01–0.1 mg/l of riboflavin, 0.1–5 mg/l of glycerol, 0.0004–0.04 mg/l of ammonium molybdate, 0.0004–0.04 mg/l of cobalt chloride, 0.001–0.1 mg/l of manganese chloride, 0.0003–0.03 mg/l of zinc sulfate, 2,000–20,000 mg/l of MOPS buffer [3-[N-morpholino]propanesulfonic acid, marketed by SIGMA under the reference M(254)], 1,000–10,000 mg/l of Tris buffer [tris(hydroxymethyl)aminomethane], marketed by SIGMA under the reference T-1503.

Advantageously, the medium of the invention contains at least 65 mg/l of alanine, 73 mg/l of arginine, 43 mg/l of asparagine, 53 mg/l of aspartic acid, 16 mg/l of cysteine, 37 mg/l of glutamine, 73 mg/l of glutamic acid, 66 mg/l of glycine, 22 mg/l of histidine, 54 mg/l of isoleucine, 84 mg/l of leucine, 89 mg/l of lysine, 33 mg/l of methionine, 44 mg/l of phenylalanine, 36 mg/l of proline, 320 mg/l of serine, 43 mg/l of threonine, 17 mg/l of tryptophan, 36 mg/l of tyrosine, 70 mg/l of valine, 0.03 mg/l of biotin, 0.03 mg/l of calcium pantothenate, 0.0008 mg/l of cyanocobalamin, 0.005 mg/l of folic acid, 0.05 mg/l of menadione, 0.15 mg/l of mesoinositol, 0.15 mg/l of nicotinamide, 0.15 mg/l of vitamin B6, 0.03 mg/l of riboflavin, 0.03 mg/l of thiamine chloride, 0.01 mg/l of lipoic acid, 1.5 mg/l of choline, 2.5 mg/l of glycerol, 5 mg/l of ethyl oxaloacetate, 0.75 mg/l of spermidine, 10 mg/l of Tween 80, 15 mg/l of adenosine, 10 mg/l of cytidine, 20 mg/l of guanosine, 6 mg/l of uridine, 750 mg/l of glucose, 500 mg/l of malic acid, 0.004 mg/l of ammonium molybdate, 0.004 mg/l of cobalt chloride, 0.016 mg/l of manganese chloride, 0.003 mg/l of zinc sulfate, 1.8 mg/l of ferric pyrophosphate, 0.25 mg/l of copper sulfate, 0.025 mg/l of boric acid, 50 mg/l of potassium sulfate, 230 mg/l of dibasic potassium phosphate, 100 mg/l of magnesium chloride, 90 mg/l of calcium chloride, 500 mg/l of ammonium chloride, 7,500 mg/l of sodium chloride, 15,000 mg/l of MOPS buffer and 7,000 mg/l of Tris buffer.

In one embodiment of the invention, the medium additionally contains at least one peptide in a concentration of between 50 and 100 mg/l or a mixture of peptides in a concentration of between 50 and 1,000 mg/l, the peptides having a length of between 4 and 15 amino acids.

In particular, the peptide is chosen from amongst the peptides having the following amino acid sequences:
Ala-Gly-Ser-Glu (SEQ ID NO: 1),
Glu-Asp-Arg-Pro-Pro-Leu-Phe-Gly-Gln-Gly-Thr-Val (SEQ ID NO: 2), and
Ala-Ser-Asp-Ala-Lys-Ala-Tyr-Asp-Thr-Glu-Val (SEQ ID NO: 3).

According to an advantageous formulation of the medium of the invention, the latter moreover comprises a beef extract whose concentration is preferably of between 2 and 10 g/l. The addition of a beef extract especially allows the growth of species such as *Staphylococcus saprophyticus*, *Xanthomonas maltophilia* and *Acinetobacter iwoffi* to be favored.

The medium of the invention can be prepared either in liquid or gel form. When it is prepared in gel form, a gelling agent is added to the medium. The gelling agent can be any known conventional gelling agent, such as gelatin, agar, agarose, etc. However, to retain the essentially synthetic nature of the medium, agarose in a concentration of approximately 10,000 mg/l is preferably chosen as gelling agent.

Of course, the components of the medium such as described above can be replaced by equivalents without this modifying the nature and the properties of the medium of the invention. Thus, the acid or base salts mentioned can be replaced by an equivalent quantity of free base or free acid or by an equivalent quantity of a salt with a different acid or base. In the same way, a free base or a free acid can be present in the form of an appropriate salt. Equally, a component defined as a hydrate can be present in an anhydrous form or be replaced by a different hydrate which will have the same properties according to criteria known per se. In the same way, an emulsifying and dispersing agent having, according to characteristics known per se, identical or similar properties to Tween 80 can be substituted for the latter.

The invention further relates to a method for determining the activity of a substance on an infectious microorganism. The method comprises adding a substance and a first microorganism to a medium according to the present invention and comparing the growth of said first infectious microorganism to the growth of a second infectious microorganism of a same type as said first infectious microorganism grown in a second medium of a same type as said first medium to which said substance has not been added.

The invention will be better understood by reading the detailed description which follows, made with reference to the annexed figures in which the abscissae represent the time in minutes and the ordinates an optical density at 650 nm in the ABBOTT MS2 apparatus.

EXAMPLE 1 composition of the medium

The medium according to the invention contains amino acids, an inorganic base, vitamins and growth factors, carbon sources, nucleosides and a buffer.

The 20 constituent amino acids of the proteins, all of the L series, with the exception of glycine, are included in the composition of the medium.

The concentration of each amino acid was determined by reference to the relative proportions of amino acids of *E. coli*, which is the best known bacterial species and the most often clinically isolated. The proportions of amino acids were estimated on the one hand by chemical analysis of a protein hydrolysate (Neidhart F. C. (1988) Chemical composition of *Escherichia coli* in *Escherichia coli* and *Salmonella typhimurium*, American Society of Microbiology, Washington D.C. vol. 1: 3–6) and on the other hand by statistical analysis of the codons of the proteins strongly expressed (Manolo G. (1987) Origine et fonction du code génétique chez *E. Coli*: structuration en banque de données et analyse statistique des séquences nucléotidiques, thèse de Doctorat ès-Sciences, Lyon [Origin and function of the genetic code in *E. coli*: structuring of data bank and statistical analysis of the nucleotide sequences, doctorate thesis in the sciences, Lyons]).

The results obtained by these two approaches are summarized in Table 1 below. The proportions relate to molar concentrations, and are given in percentage of amino acids.

TABLE 1

| | Ala | Arg | Asx | Cys | Glx | Gly | His | Ile | Leu | Lys | Met | Phe | Pro | Ser | Thr | Trp | Tyr | Val |
|---|---|---|---|---|---|---|---|---|---|---|---|---|---|---|---|---|---|---|
| (1) | 9.6 | 5.5 | 9.0 | 1.7 | 9.8 | 11.5 | 1.8 | 5.4 | 8.4 | 6.4 | 2.9 | 3.5 | 4.1 | 4.0 | 4.7 | 1.1 | 2.6 | 7.9 |
| (2) | 10.6 | 6.8 | 9.6 | 0.5 | 10.5 | 8.6 | 1.6 | 5.7 | 7.1 | 7.8 | 2.3 | 3.1 | 3.2 | 4.2 | 5.5 | 0.5 | 2.6 | 8.8 |

(1) refers to the chemical analysis of a protein hydrolysate.
(2) corresponds to the statistical analysis of the codons of the strongly expressed proteins.

Glx and Asx respectively refer to a glutamic acid-glutamine and aspartic acid-asparagine mixture.

The acid and amine forms of these amino acids were distinguished with the method of Manolo. The relative proportions given as percentages are the following: Glu 7.0%, Gln 3.5%, Asp 5.5%, Asn 4.1%. The proportions between the molar concentrations of the different amino acids retained are those which were determined by the method of Neidhart, with the exception of the ratios Glu/Gln and Asp/Asn, which are respectively 2 and 1.3, determined by the method of Manolo.

The proportions in percentage of amino acids of the medium on the base of the molar concentrations are summarized in Table 2 below.

TABLE 2

| Ala | Arg | Asn | Asp | Cys | Gln | Gly | His | Ile | Leu | Lys | Met | Phe | Pro | Ser | Thr | Trp | Tyr | Val |
|---|---|---|---|---|---|---|---|---|---|---|---|---|---|---|---|---|---|---|
| 9.6 | 5.5 | 3.8 | 5.2 | 1.7 | 3.3 | 6.5 | 11.5 | 1.8 | 5.4 | 8.4 | 6.4 | 2.9 | 3.5 | 4.1 | 4.0 | 4.7 | 1.1 | 2.6 | 7.9 |

Figure 1:
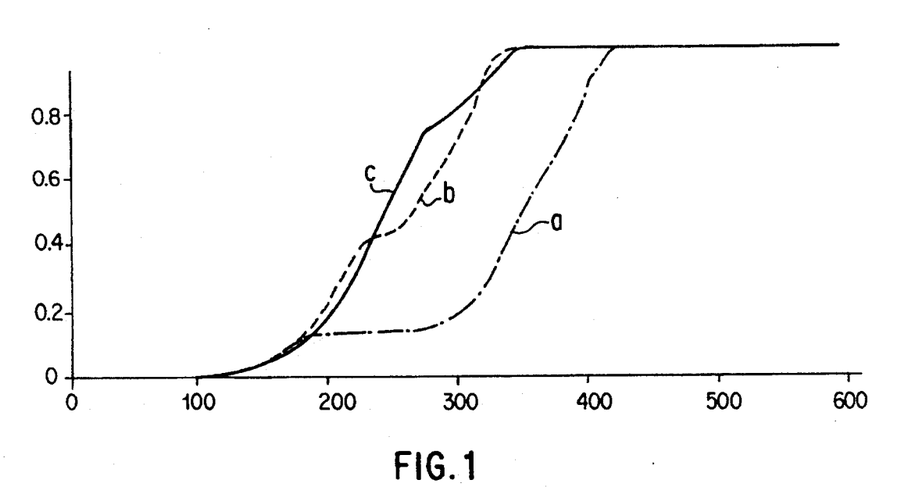
FIG. 1 shows the effect of an increase in the concentration of serine in the medium of the invention symbolized by IST, in comparison with the growth obtained with the Mueller-Hinton medium marketed by DIFCO LABORATORIES under the reference 0757-01-4. Curve a represents the growth obtained with the IST medium having an initial concentration of serine of 32 mg/l. Curve b represents the growth with the IST medium for a concentration of serine increased by a factor of 10. Curve c represents the growth obtained with the Mueller-Hinton medium.
Figure 2:
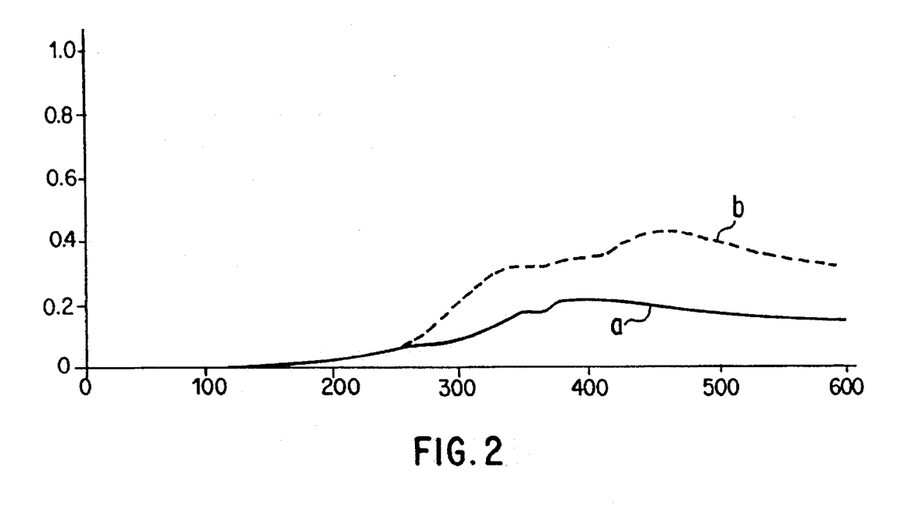
FIG. 2 represents the effect of the concentration of amino acids in the IST medium on the growth of *Pseudomonas aeruginosa*; a illustrates the growth obtained with the initial concentration of the different amino acids of 108 mg/l, and b shows the effect of an increase in the concentration of amino acids by a factor of 3.

The qualitative and quantitative composition of amino acids was then optimized for the different species in order to obtain growth in conformity with that obtained with the reference Mueller-Hinton medium. In particular, the serine concentration was increased to obtain a final concentration of near to 400 mg/l, advantageously 320 mg/l, because this amino acid is very rapidly assimilated by Serratia, in particular the species marcescens, liquefaciens and fonticola and the species *Morganella morganii, Proteus mirabilis* and *Yersinia enterocolitica*. The improvement in the growth is obtained by increasing the final concentration of serine, especially for *Serratia marcescens*, as illustrated in FIG. 1. As emerges from this figure, an increase of a factor of 10 in the concentration of serine allows a bacterial growth to be obtained near to that obtained with Mueller-Hinton medium. The final concentrations of amino acids were defined, after having verified their importance on the final biomass, taking account of the biomass obtained in Mueller-Hinton medium. This study is especially well illustrated with *Pseudomonas aeruginosa*, whose growth and final biomass depend strongly on the concentration of amino acids, as shown in FIG. 2.

The inorganic base contains metallic ions and salts whose role has been described by Gottschalk G. (Bacteriol. Metabolism, 2nd Edition, page 3, Spring Verlag., Berlin (1988)). The metallic ions are boron, cobalt, copper, iron, manganese, molybdenum and zinc, which play the role of enzymatic cofactors. The concentrations chosen for these ions are those defined by Neidhart (Neidhart C. et al., Culture Medium for Enterobacteria, Journal of Bacteriology, Sept. Pages 736–747 (1974)). With the exception of iron, the omission of the other oligoelements does not cause any significant effect on the growth of the bacteria tested because the dosages achieved have shown that these elements are contributed indirectly and in sufficient quantity by the other commercially available constituents of the medium. Of course, in assuming the obtainment of increasingly pure commercial products, it is preferred to maintain a controlled supply of the mineral ions in order to ensure a minimum concentration which is always compatible with the growth of bacteria. On the contrary, iron proves to be an indispensible additional constituent, especially for the growth of certain species. The concentration of the iron in the medium, which is relatively high, was optimized to satisfy the requirements of *P. aeruginosa* and of the staphylococci without inhibiting the growth of the other species. By way of example, different iron salts can be included in the medium, such as ferric pyrophosphate, ferric chloride, ferric citrate and ferric sulfate, independently or in combination. Preferably, the constituent of the invention is the pyrophosphate salt.

The sulfur is essentially supplied by the sulfate ion, which represents 45% of the sulfur present in the medium, but certain bacteria which have lost their capacity to reduce the sulfate ion might be able to use other reduced compounds present in the medium, especially cysteine and methionine. Preferably, the sulfate ion of the medium of the invention is potassium sulfate. The concentration of sulfate chosen is that defined by Neidhart.

The principle source of potassium (70%) and of phosphorus (100%) is supplied by dibasic potassium phosphate.

The concentration of phosphate was determined in order to avoid the formation of precipitates with calcium and magnesium ions affecting the optical quality of the medium and modifying the concentrations of these two ions. The chosen concentration is that defined by Neidhart.

The ammonium ion forms a source of nitrogen utilized by the majority of the bacteria. The concentration of ammonium ions was defined taking account of the concentrations of amino acids, which are likewise used as a source of nitrogen by the bacteria. The chloride form is preferred, especially in relation to phosphate forms, this being to avoid a supplementary supply of phosphate ions.

Calcium and magnesium ions are the cofactors of numerous enzymes and are known to modify the sensitivity to certain antibiotics, especially the aminosides with respect to Pseudomonas (Christe M. et al. (1982) Susceptibilité du *Pseudomonas aeruginosa* aux aminosides [susceptibility of *Pseudomonas aeruginosa* to aminosides]: influence of calcium and of magnesium, Schweizerische Medizinische Wochenschrift, 112, 4, 241). The contents of calcium and magnesium ions of the medium of the invention correspond to standards recognized for the antibiogram by the NCCLS (National Committee for Clinical Laboratory Standards, 1990, Methods for dilution antimicrobial susceptibility tests for bacteria that grow aerobically. Approved standard publication M7-A2: 10–11 Villanova Pa. U.S.A.). The concentrations by weight of calcium and magnesium ions are respectively 25 and 12.5 mg/l. The calcium chloride and magnesium chloride forms are advantageously chosen in the constituents of the medium of the invention.

Figure 3:
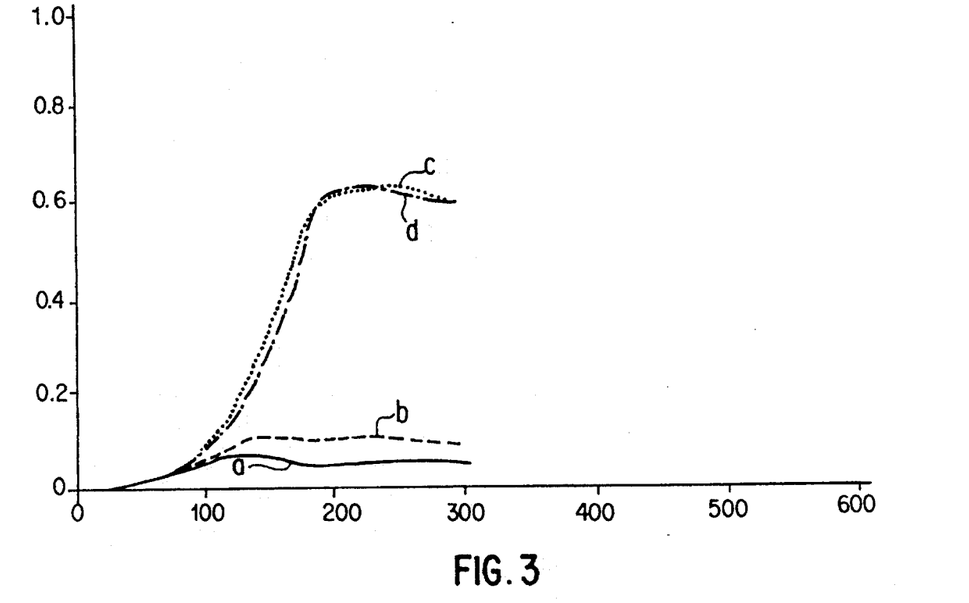
FIG. 3 shows the influence of the concentration of sodium chloride in the IST medium on the growth of *Proteus mirabilis*; a, b, c and d illustrate this influence on respective NaCl concentrations of 0.3%, 0.5%, 1% and 0.75%.
Figure 4:
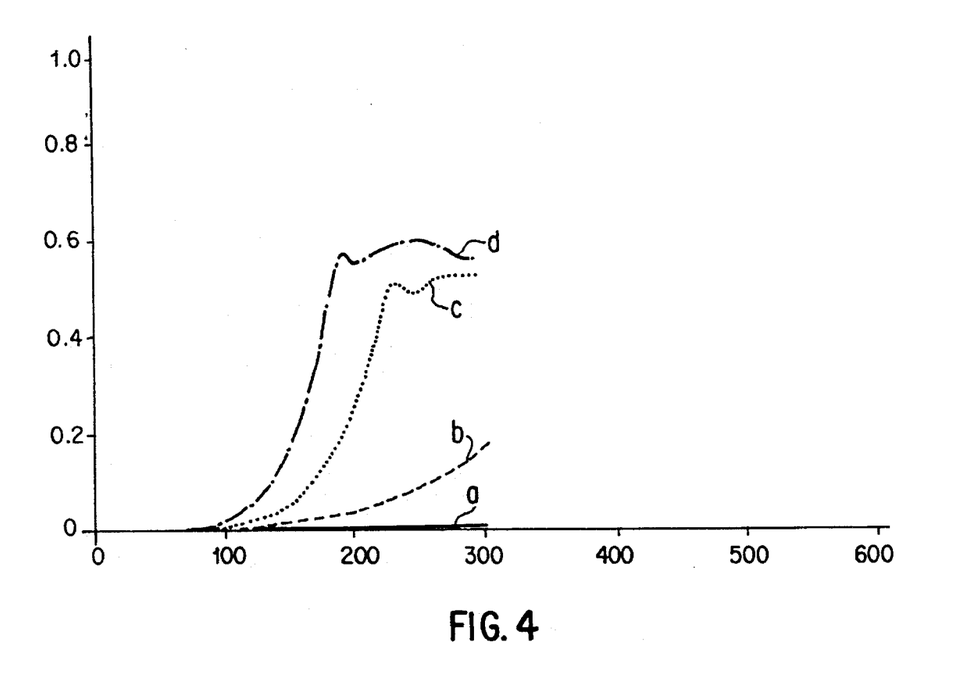
FIG. 4 illustrates the influence of the sodium chloride concentration in the IST medium on the growth of *Vibrio parahaemolyticus*; a, b, c and d correspond to respective concentrations of NaCl of 0.3%, 0.5%, 0.75% and 1%.
Figure 5:
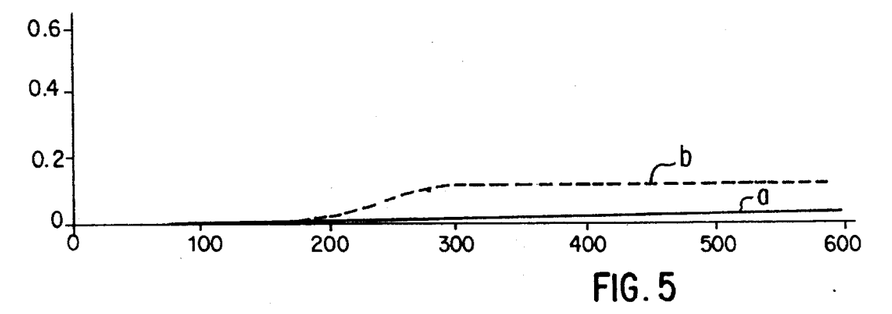
FIG. 5 illustrates the effect of folic acid on the growth of *Enterococcus faecium*. Curve a represents the results obtained without folic acid, and curve b represents the growth obtained with addition to the IST medium of 0.005 mg/l of folic acid.

Sodium chloride represents the principle source of sodium and chloride ions. The concentration of NaCl was optimized taking account of the high sodium requirements of *Proteus mirabilis* and of *Vibrio parahaemolyticus*, as shown in FIGS. 3 and 4.

The vitamins and growth factors are important constituents for the metabolism of bacteria. The role of vitamins B1, B2, B5, B6, B12, H and nicotinamide in bacterial metabolism is specified in several works, including the "Manual of Methods for General Bacteriology" of Guirard and Snell (Biochemistry Factors in Growth, chapter 7 (1981)). Mesoinositol, choline and glycerol are precursors of cellular lipids, including the membrane phospholipids (see Klig L. S. et al. (1990) Phospholipid biosynthesis in Candida albicans: regulation by the precursors inositol and choline, J. Bact. 178(8): 4407–4414). The concentrations of folic acid, lipoic acid, spermidine, ethyl oxaloacetate and Tween 80 were particularly well studied for the medium of the invention.

Figure 12:
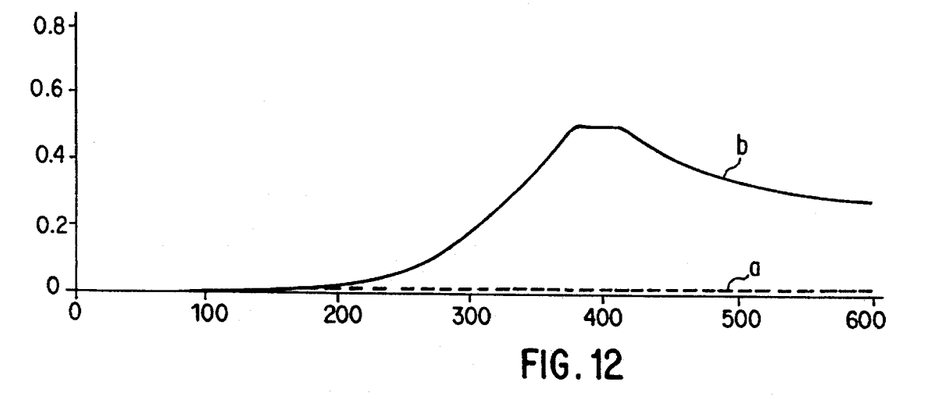
FIGS. 12 and 13 illustrate the compatibility at a determined concentration of the folic acid with the activity of certain antibiotics. They show the growth of *Enterococcus faecalis* respectively on the IST medium of the invention and on the Mueller-Hinton medium without antibiotic (curves b) and in the presence of an antibiotic, trimethoprim at a concentration of 0.25 mg/l (curves a). These figures confirm the inhibition of the growth of this strain, whatever the medium, by a concentration of 0.25 mg/l of trimethoprim.
Figure 13:
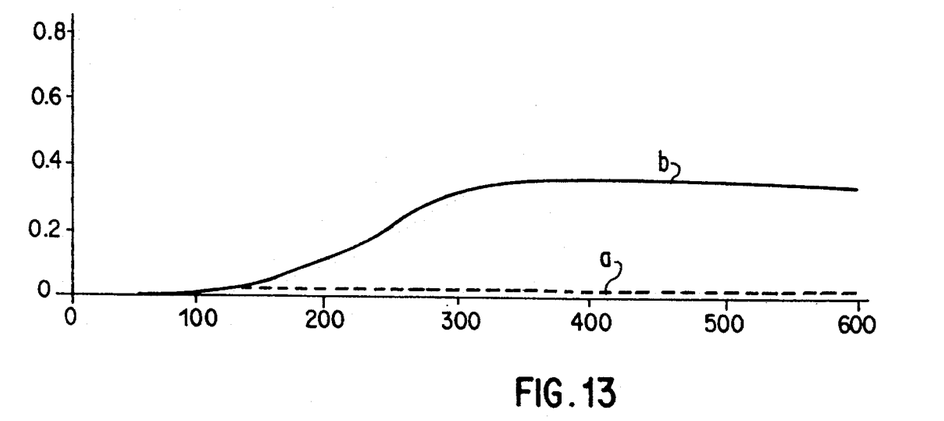

Folic acid is a coenzyme whose importance for the growth of enterococci, especially for the different strains of *E. faecalis, E. faecium and E. hirae*, has been demonstrated, as described below. It is moreover known to affect the activity of the sulfamides and trimethoprim family (Then R. et al., Mécanisme moléculaire de la bactéricidie; sulfamides et trimethoprime [Molecular mechanism of bactericidal activity; sulfamides and trimethoprim]. Bactéricidie 1990, Editions Maloine, Paris). The concentration of folic acid was determined to satisfy the requirements of the strains tested and for its compatibility with the activity of the antibiotics, as illustrated in FIGS. 12 and 13.

Figure 6:
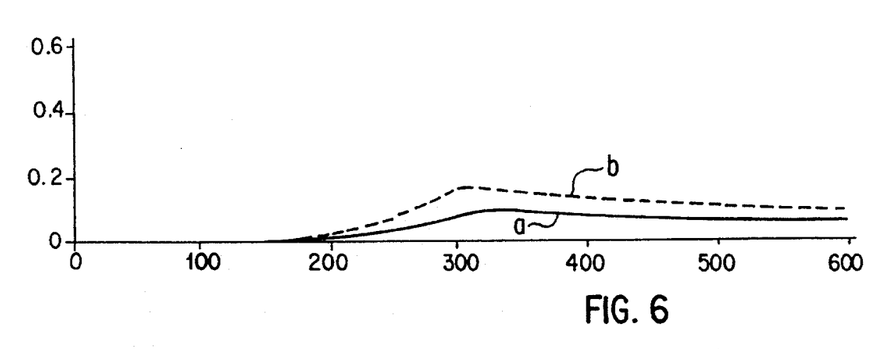
FIG. 6 shows the effect of lipoic acid on the growth of *Enterococcus faecalis*, curve a showing the results obtained with an IST medium devoid of lipoic acid and curve b illustrating the growth of this strain after addition to the IST medium of lipoic acid at a concentration of 0.01 mg/l.

The concentration of lipoic acid was determined as the minimum concentration allowing the growth of the enterococci and of the streptococci of group B to be increased to a maximum. FIG. 6 illustrates the effect of lipoic acid on the growth of *Enterococcus faecalis*.

Figure 7:
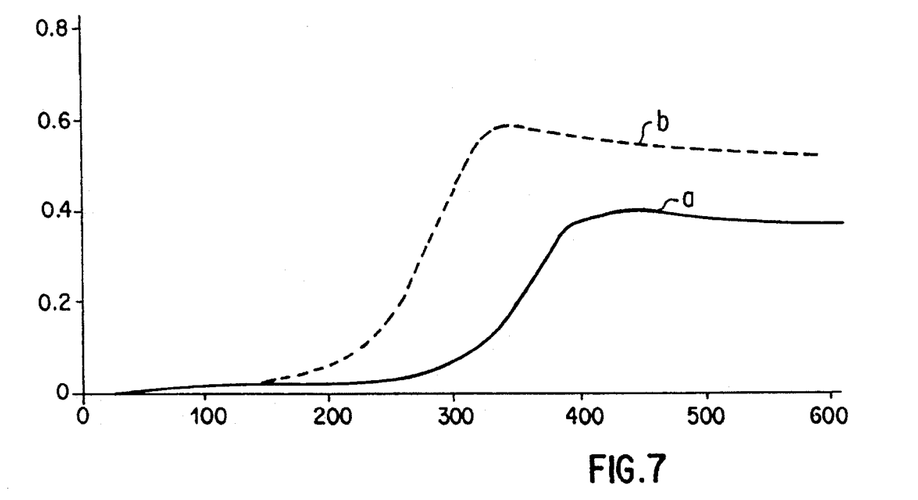
FIG. 7 shows the effect of spermidine on the growth of *Proteus mirabilis*. a shows the results obtained with the IST medium devoid of spermidine and b the growth obtained after addition of 0.25 mg/l of spermidine.

The polyamines are present in the eukaryotic and prokaryotic cells and participate in numerous biological reactions including the synthesis of nucleic acids and of proteins (see Tabor C. W. and Tabor H. (1985) Polyamines in Microorganisms, Microbiol. Rev. 49: 81–99). Putrescine, spermine and spermidine were tested. Spermidine was chosen according to the results, especially for the growth of Proteus, Morganella, Providencia and Serratia, at a preferential concentration of 0.75 mg/l. FIG. 7 illustrates the effect of spermidine on the growth of *Proteus mirabilis*.

Figure 8:
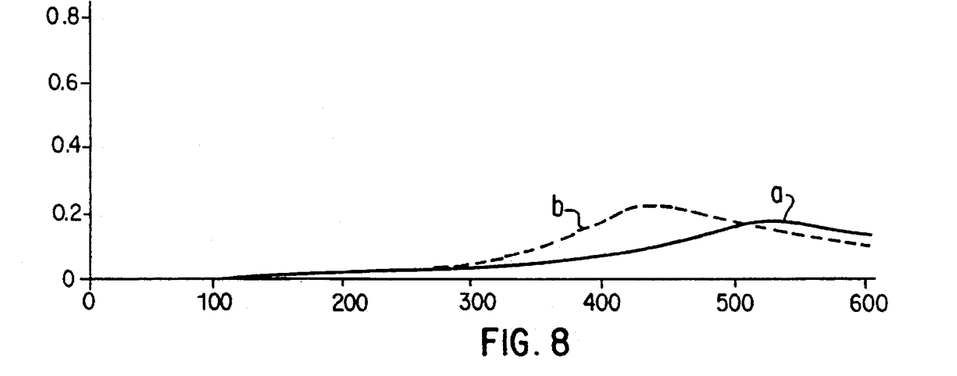
FIG. 8 illustrates the effect of ethyl oxaloacetate on the growth of *Staphylococcus saprophyticus*. a shows the growth obtained with an IST medium devoid of ethyl oxaloacetate, and b shows the results obtained with 5 mg/l of ethyl oxaloacetate.

Ethyl oxaloacetate is described for its stimulatory effect on the growth of numerous species (Pelczar M. J. and Brown J. H. (1951) Synthetic culture media for reference use in dairy bacteriology, J. Milk Food Technol., 14: 90–91 and 97). Its influence on the growth of the strains of staphylococci was demonstrated, as shown in FIG. 8, and the concentration taken is that allowing the growth of the staphylococci to be increased without inhibiting that of the other species.

Figure 9:
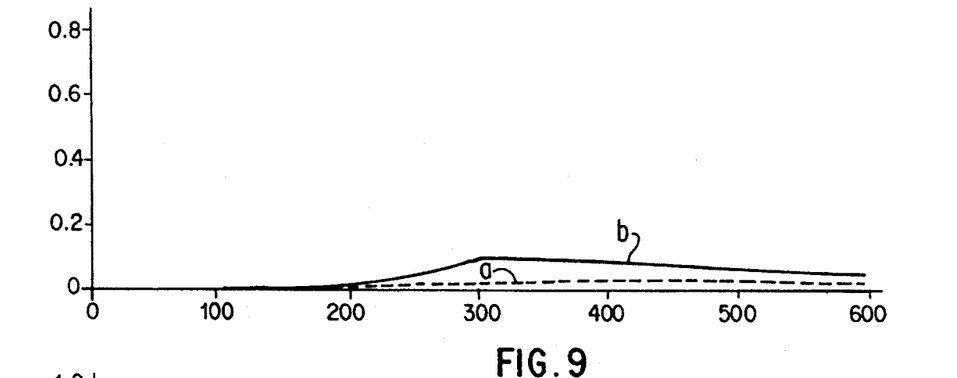
FIG. 9 shows the effect of the removal of Tween 80 on the growth of *Enterococcus faecalis*. Curve a shows the growth obtained with an IST medium devoid of Tween 80 and curve b the results after addition 10 mg/l of Tween 80.

Tween 80 is an emulsifying and dispersing agent. It is able to replace biotin as shown by Gretler A. C. et al. Vitamin nutrition of the staphylococci with special reference to their biotin requirements (1954) J. Bact. 70: 44–49). It also plays a detoxifying and protective role by absorbing the possible toxic metabolite elements of the medium (see Klein R. D. et al. (Simplified media for growth of haemophilus influenzae for clinical and normal flora sources. Journal of General Microbiology. 113: 409–411 (1979)). As shown in FIG. 9, the omission of Tween 80 in the medium causes a decrease in growth of the different bacterial species.

Figure 10:
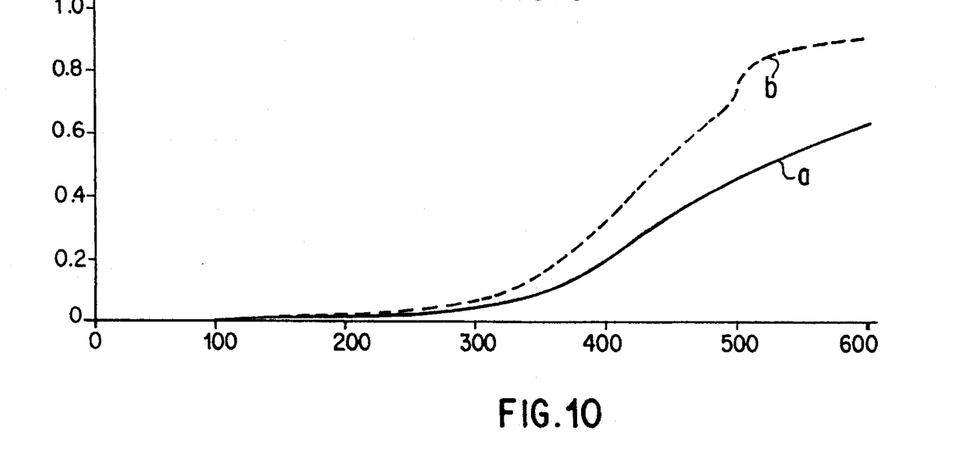
FIG. 10 shows the effect of L-malic acid on the growth of *Alcaligenes faecalis*. Curve a shows the growth obtained with IST medium devoid of L-malic acid and curve b the results after addition of a concentration of 500 mg/l of L-malic acid.
Figure 11:
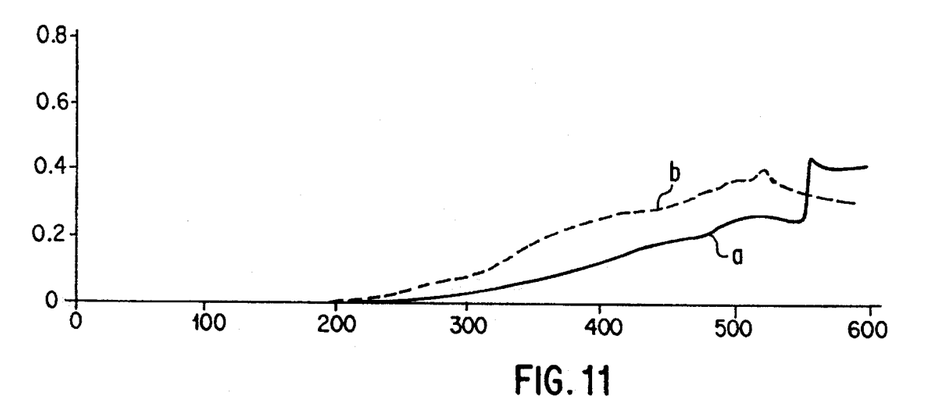
FIGS. 11 illustrates the effect of L-malic acid on the growth of *Pseudomonas aeruginosa*, curve a corresponding to the growth obtained with an IST medium devoid of L-malic acid and curve b after addition of a concentration of 500 mg/l of L-malic acid.

The carbon sources of the medium of the invention are mainly represented by a sugar, preferably D-glucose, and an organic acid, in particular L-malic acid. D-glucose has been retained, taking account of its utilization by a large number of bacterial species with fermentative or non-fermentative metabolism (Stanier R. Y. et al. (1966) The aerobic Pseudomonas: a taxonomic study. J. Gen. Microbiol. 43: 159–271). Its concentration in the medium of the invention was determined to obtain a biomass close to that obtained with the reference Mueller-Hinton medium. L-malic acid is necessary for the growth of the non-saccharolytic species, such as *Alcaligenes faecalis*, as shown in FIG. 10, and *Pseudomonas acidovorans*. It also increases the growth of *Pseudomonas aeruginosa* which utilizes it preferentially to glucose as a carbon source, as shown in FIG. 11. The respective concentrations of D-glucose and L-malic acid were determined to correspond to the qualities of Mueller-Hinton.

The purine and pyrimidine bases can be supplied in several forms, that is to say in the form of precursors, of free bases, of nucleosides or of nucleotides. The studies on the medium of the invention have shown that the supply of the two hypoxanthine and uracil precursors does not satisfy the base requirements of the enterococci. Moreover, the nucleotides cause a decrease in the growth of numerous bacterial species. Significant increases have been obtained with the nucleosides, in the absence of thymidine taking account of its incompatibility with the activity of the sulfamides and of trimethoprim. The proportions between purines and pyrimidines were defined in relation to those described for the synthesis of RNA by Neidhart (Neidhart et al. (1990) Physiology of the bacterial cell. A molecular approach. Sinauer associates, inc. U.S.A.), taking account of the absence of thymidine, that is to say purines/pyrimidines in a ratio of between 1.5 and 2.2 and advantageously of 1.8. The final concentrations were then optimized essentially to satisfy the growth of the staphylococci and of the enterococci.

The buffer was chosen to meet the requirements of optical quality of the medium and of pH, the pH of 7.4 being suited to the antibiogram and to the growth of the bacteria. The acid form is supplied by the MOPS buffer, which was particularly chosen on account of its pKa of 7.2 (at 20° C.) close to the pH of the medium. The concentration of the MOPS buffer was defined in order to ensure a buffer power equivalent to that of the Mueller-Hinton medium without exceeding the concentration of 80mM, above which inhibitions of bacterial growth were described by Neidhart. The basic form particularly retained is Tris buffer, which was preferred to a strong base like sodium hydroxide in order to avoid a supplementary supply of ions. The concentration in the medium of the invention was defined as a function of that of the MOPS buffer and of the final pH desired.

Figure 14:
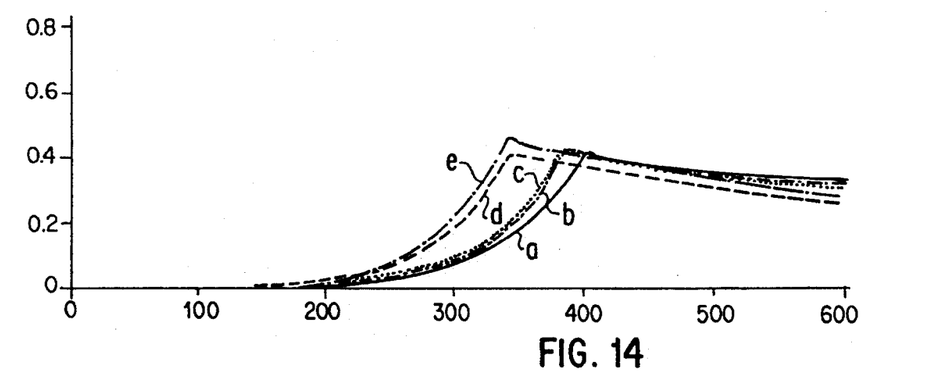
FIG. 14 shows the influence of the addition of the peptide Ala-Gly-Ser-Glu (SEQ. ID NO: 1) to the IST medium of the invention and the comparison with the results obtained by the addition of constituent free amino acids of this peptide. Curve a corresponds to the results obtained with the medium of the invention without addition of the abovementioned peptide, nor addition of constituent free amino acids of this peptide. Curve b illustrates the results obtained with the addition of amino acids Ala, Gly, Ser, GLu respectively at concentrations of 11, 9, 12.5 and 17.5 mg/l. Curve c shows the results obtained with the addition of amino acids Ala, Gly, Ser, Glu respectively at concentrations of 22, 18, 25 and 35 mg/l. Curve d corresponds to the bacterial growth obtained after addition to the medium of 50 mg/l of the peptide. Curve e illustrates the results obtained after addition of 100 mg/l of the same peptide.

The Applicant has moreover demonstrated that the addition of peptides to the medium of the invention had a stimulator effect, especially for the growth of the enterococci. Among the peptides tested, only those showing size a less than or equal to 15 amino acids cause a strong increase in the growth. Moreover, the Applicant has shown that the addition of the free amino acid constituents of the peptides, supplied in equivalent concentration, does not allow the stimulatory effect to be reproduced, as illustrated in FIG. 14. In particular, the tetrapeptide Ala-Gly-Ser-Glu (SEQ ID NO: 1) causes a considerable increase in the growth of different strains of *Enterococcus hirae* and *Enterococcus faecium*, other peptides such as Glu-Asp-Arg-Pro-Pro-Leu-Phe-Gly-Gln-Gly-Thr-Val (SEQ ID NO: 2) and Ala-Ser-Asp-Ala-Lys-Ala-Tyr-Asp-Thr-Glu-Val (SEQ ID NO: 3) giving interesting results for other strains of Enterococci.

EXAMPLE 2

Preparation of the medium of the invention

The medium according to the invention can be prepared, for example, from six concentrated parent solutions which are obtained directly from commercial constituents in powder form, referenced in the SIGMA catalog, diluted with a required quantity of distilled water. The solutions are then sterilized by filtration and refrigerated in liquid or frozen form at −20° C. The parent solutions, which are respectively inorganic base solutions (5×concentrated), oligoelements (10,000×concentrated), amino acids (3×concentrated), nucleosides (8×concentrated), water-soluble vitamins (700× concentrated), lipid-soluble vitamins (2,000×concentrated), are next mixed with one another and then diluted with a required quantity of distilled water and glucose, L-malic acid and dibasic potassium phosphate (constituents marketed by SIGMA) are added. If necessary, the pH is adjusted by addition of sodium hydroxide or hydrochloric acid to obtain a value close to 7.4. The order in which the different constituents are mixed is not critical.

EXAMPLE 3

Comparison of the results obtained with the medium of the invention and the reference Mueller-Hinton medium.

With the determination of the sensitivity to antibiotics in mind, a suspension of 0.5 MF (Mac Farland) in physiological water was prepared from bacterial colonies selected in Petri dishes, reading being carried out on an ATB 1550 densitometer marketed by BIOMERIEUX (ATB trade mark). The suspension obtained was respectively diluted to 1/100th in the medium of the invention and Mueller-Hinton medium. VITEK cards (VITEK trade mark) containing different antibiotics at 10 concentrations were filled in vacuo into a VITEK apparatus marketed by BIOMERIEUX-VITEK. The cards were incubated for 12 hours in a VITEK incubator/reader marketed by BIOMERIEUX-VITEK. The growth kinetics were visualized and interpreted and an equivalent MIC was determined (equivalent MIC: equivalent minimum inhibitory concentration, that is to say the smallest concentration for which no bacterial growth is detected by the apparatus).

The results have been shown in Tables 3 and 4 below.

IST refers to the medium of the invention and MH signifies Mueller-Hinton medium.

TABLE 3

Results on gram-negative bacteria

| Antibiotics concentration in mg/l | Strains | Equivalent MIC IST | Equivalent MIC MH | NCCLS Category IST | NCCLS Category MH |
|---|---|---|---|---|---|
| ceftazidim | *E. coli* | | | | |
| [0.06 → 64]* | CDC 2008 | <0.06 | <0.06 | S | S |
| | CDC 2254 | 0.5 | 1 | S | S |
| | *S. marcescens* | | | | |
| | CDC 2102 | 0.5 | 0.25 | S | S |
| | CDC 2162 | 2 | 2 | S | S |
| | CDC 2240 | 0.5–1 | 1 | S | S |
| | *P. aeruginosa* | | | | |
| | AP 9 | 32 | 32 | R | R |
| | AP 13 | 4 | 4 | S | S |
| | CDC 2275 | 4 | 4 | S | S |
| | ATCC 27853 | 1 | 2 | S | S |
| piperacillin | *K. pneumoniae* | | | | |
| [1 → 256]* | CDC 2174 | 8 | 8 | S | S |
| | CDC 2182 | 16 | 32 | S | I |
| | AP 14 | 64 | 256 | I | R |
| | *S. marcescens* | | | | |
| | CDC 2021 | 2 | 2 | S | S |
| | CDC 2162 | >256 | >256 | R | R |
| | *P. aeruginosa* | | | | |
| | AP 8 | 4 | 4 | S | S |
| | AP 13 | 8–16 | 16 | S | S |
| ticarcillin + clavulanic | *E. cloacae* | | | | |
| acid | CDC 2013 | 64/2 | 128/2 | I | R |
| [1/2 → 256/2]* | CDC 2129 | 2/2 | 2/2 | S | S |
| | *E. coli* | | | | |
| | CDC 2084 | 4/2–8/2 | 8/2 | S | S |
| | CDC 2111 | 32/2– | 32/2– | I | I |
| | CDC 2259 | 64/2 256/2 | 64/2 >256/2 | R | R |
| | *P. aeruginosa* | | | | |
| | CDC 2099 | 128/2 | 128/2 | R | R |
| | AP 8 | 8/1–16/2 | 16/2 | S | S |
| | AP 13 | 64/2 | 128/2 | S | S |
| gentamicin | *K. pneumoniae* | | | | |
| [0.125 → 64]* | CDC 2177 | 0.5 | 0.25 | S | S |
| | CDC 2249 | 8 | 8 | I | I |
| | CDC 2279 | 4 | 4 | S | S |
| | *P. aeruginosa* | | | | |
| | CDC 2009 | 16–32 | 32 | R | R |
| | CDC 2239 | 2 | 2 | S | S |
| | CDC 2257 | 0.5–1 | 0.5 | S | S |
| ofloxacin | *K. pneumoniae* | | | | |
| [0.125 → 32]* | CDC 2279 | 0.25 | 0.25 | S | S |
| | API 88.03.111 | 1 | 1 | S | S |
| | API 88.08.056 | 4 | 4 | I | I |
| | *S. marcescens* | | | | |
| | API 81.45.111 | 4 | 2 | I | S |

TABLE 3-continued

Results on gram-negative bacteria

| Antibiotics concentration in mg/l | Strains | Equivalent MIC | | NCCLS Category | |
|---|---|---|---|---|---|
| | | IST | MH | IST | MH |
| trimethoprim + sulfa- | API 81.47.110 *E. coli* | 16 | 8 | R | R |
| methoxazole | UA 200 | <0.25/4.75 | <0.25/4.75 | S | S |
| [0.25–4.75 → 128/2432]* | API 84.03.115 *K. pneumoniae* | 128/2432 | 128/2432 | R | R |
| | CDC 2174 | <0.25/4.75 | <0.25/4.75 | S | S |
| | CDC 2280 | 128/2432 | 128/2432 | R | R |

TABLE 4

Results on gram-positive bacteria

| Antibiotics concentration in mg/l | Strains | Equivalent MIC | | NCCLS Category | |
|---|---|---|---|---|---|
| | | IST | MH | IST | MH |
| trimethoprim + sulfa- | *S. aureus* | | | | |
| methoxazole | ATCC 29213 | <0.06 | <0.06 | S | S |
| [0.06/1.14 → 32/608]* | CDC 2215 | 0.12 | 0.12 | S | S |
| | CDC 2194 | <0.06 | <0.06 | S | S |
| | *S. epidermidis* | | | | |
| | CDC 2024 | <0.06 | <0.06 | S | S |
| | CDC 2234 | 16 | 32 | R | R |
| | CDC 2105 | 0.25 | 0.25 | S | S |
| vancomycin | *S. aereus* | | | | |
| [0.5 → 32]* | ATCC 29213 | 2 | 2 | S | S |
| | CDC 2215 | 2 | 1 | S | S |
| | CDC 2194 | 2 | 1 | S | S |
| | *S. epidermidis* | | | | |
| | CDC 2024 | 4 | 4 | S | S |
| | CDC 2234 | 2 | 2 | S | S |
| | CDC 2105 | 4 | 2 | S | S |
| | *E. faecalis* | | | | |
| | CDC 2017 | 8 | 16 | I | I |
| | CDC 2230 | 1 | 1–2 | S | S |
| | CDC 2225 | 4 | 4 | S | S |
| erythromicin | *S. aureus* | | | | |
| [0.06 → 32]* | ATCC 29213 | 0.5 | 0.25 | S | S |
| | CDC 2215 | 0.5 | 0.5 | S | S |
| | CDC 2194 | >32 | >32 | R | R |
| | *S. epidermidis* | | | | |
| | CDC 2024 | 0.5 | 0.25 | S | S |
| | CDC 2234 | >32 | >32 | R | R |
| | CDC 2105 | 0.25 | 0.25 | S | S |
| | *E. faecalis* | | | | |
| | CDC 2073 | 16 | 16 | R | R |
| | CDC 2230 | 4 | 4 | I | I |
| oxacillin | *S. aureus* | | | | |
| [0.5 → 16]* | ATCC 29213 | <0.25 | <0.25 | S | S |
| | CDC 2215 | 1 | <0.5 | S | S |
| | CDC 2194 | 1 | <0.5 | S | S |
| | *S. epidermidis* | | | | |
| | CDC 2234 | 2 | 4 | S | R |

*A range of concentration, of ratio 2, was tested for each antibiotic in each of the abovementioned concentration margins.

S, I and R respectively signify "sensitive", "intermediate" and "resistant" with reference to the critical concentrations defined by the NCCLS (National Committee for Clinical Laboratory Standards).

CDC: Center for Disease Control (Atlanta, United States).

UA and AP: Collection of Strains described by Flandrois J. P. et al. "Antibiogramme automatisé" [Automated antibiogram] (1988) 1st edition, Walter Coussement—Brussels.

ATCC: American Type Culture Collection (USA).

API: BIOMERIEUX strain collection.

As is evident from the tables above, there is an agreement of the results apart from more or less one dilution, which demonstrates the equivalence of the two media as far as the study of the antibiotics is concerned. Moreover, the results show that the medium of the invention allows strains to be detected which show a feature of resistance to the antibiotics.

EXAMPLE 4

Comparison between the medium of the invention and the medium described in the Patent EP-0 019 054.

The prior art medium had been initially made following the procedure described by Hall (Hall M. J. et al., Roche susceptibility test (RST) medium, a defined formulation for susceptibility testing II, Manufacture stability and use, Journal of Microbiological Method 2: 215–220 (1984)). The process, however, had to be slightly modified taking account of the precipitation of the solution containing the amino acids, the magnesium glycerophosphate and the calcium gluconate.

Comparison of the bacterial growth:

The strains respectively tested are enterobacteria, *Pseudomonas aeruginosa*, staphylococci, enterococci and streptococci of group B.

A suspension was prepared from colonies isolated on agar and adjusted to 0.5 MF in physiological water (ATB 1550 densitometer). The suspension was diluted to 1/10th in physiological water, then rediluted to 1/10th respectively in RST medium and the IST medium of the invention, which had previously been divided into 1 ml per cuvette in the cassettes of the MS2 apparatus (marketed by ABBOTT). The cassettes were incubated for 10 hours and a reading was carried out every 5 minutes.

Figure 15:
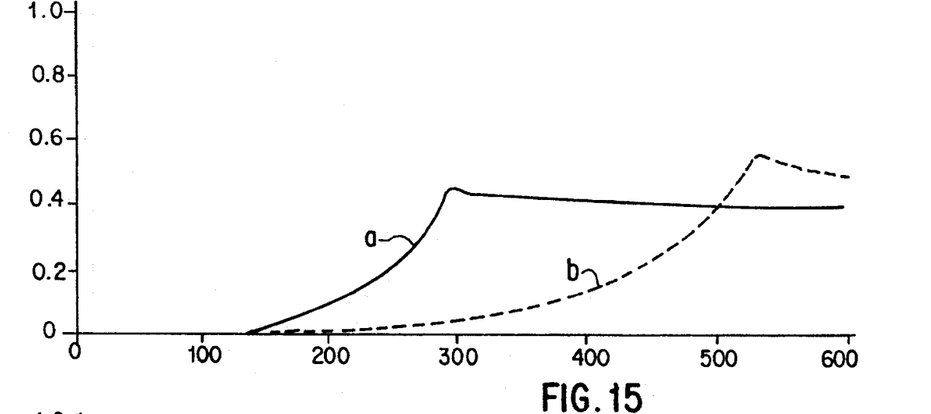
FIG. 15 illustrates the comparison between the growth of a strain of *S. agalactiae* with the IST medium of the invention (curve a) and the prior art medium (Mueller-Hinton) (curve b).

As illustrated in FIG. 15, a more rapid growth of the streptococci of group B is observed with the medium of the invention in comparison with the RST medium, which of course allows a reading of the antibiogram after 5 hours' incubation by kinetic analysis of the growth, against approximately 9 hours with the prior art medium.

Figure 16:
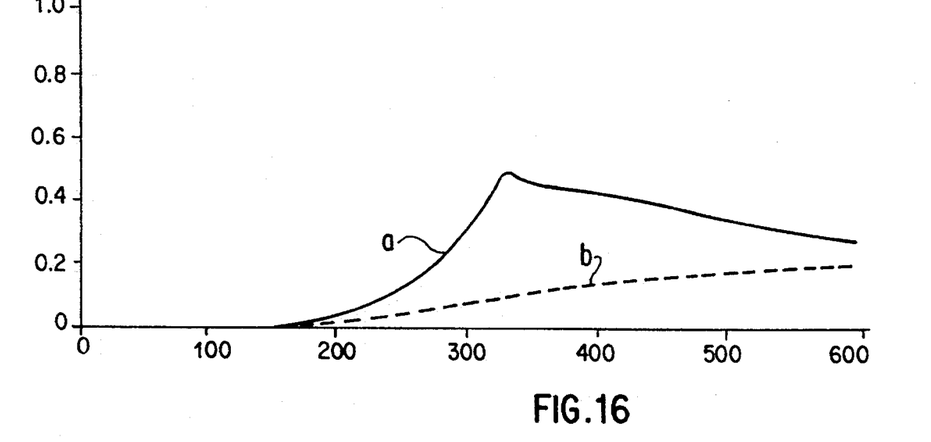
FIG. 16 establishes the comparison of the growth of a strain of *E. faecium* with the medium of the invention (curve a) and the prior art medium (curve b).
Figure 17:
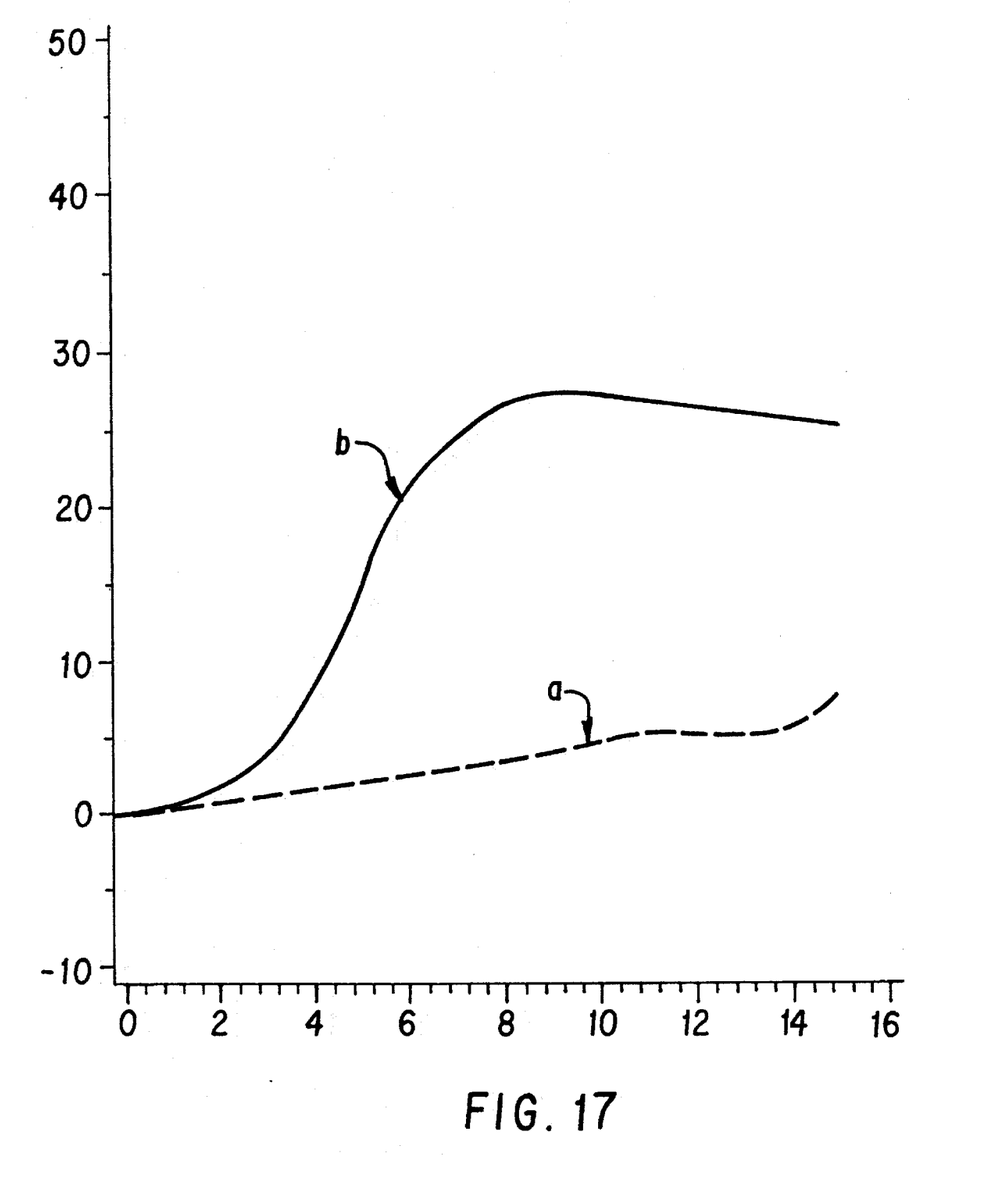
FIG. 17 illustrates the influence of the incorporation of a beef extract in the IST medium on the growth of *Staphylococcus saprophyticus*. a represents the growth obtained with an IST medium devoid of beef extract, and b represents the results obtained with 5 g/l of beef extract.

In the same way, the growth kinetics of the enterococci with the medium of the invention enables an antibiogram result to be produced in approximately 5 hours, these same bacteria growing with difficulty with the medium of the prior art. This is well illustrated in FIG. 16, which gives a comparison of the growth of a strain of *E. faecium* with the IST and RST media.

I claim:

1. Nutritive medium for the culture of microorganisms, characterized in that it contains 7–70 mg/l of alanine, 8–80 mg/l of arginine, 5–50 mg/l of asparagine, 6–60 mg/l of aspartic acid, 2–20 mg/l of cysteine, 4–40 mg/l of glutamine, 8–80 mg/l of glutamic acid, 7–70 mg/l of glycine, 2.5–25 mg/l of histidine, 6–60 mg/l of isoleucine, 9–90 mg/l of leucine, 9–90 mg/l of lysine, 4–40 mg/l of methionine, 5–50 mg/l of phenylalanine, 4–40 mg/l of proline, 4–400 mg/l of serine, 5–50 mg/l of threonine, 2–20 mg/l of tryptophan, 4–40 mg/l of tyrosine, 8–80 mg/l of valine, 0.01–0.2 mg/l of biotin, 0.01–0.3 mg/l of calcium pantothenate, 0.001–0.01 mg/l of folic acid, 0.01–0.5 mg/l of inositol, 0.04–0.2 mg/l of nicotinamide, 0.02–0.3 mg/l of vitamin B6, 0.01–0.1 mg/l of thiamine chloride, 0.005–0.05 mg/l of lipoic acid, 0.1–5 mg/l of choline, 1–10 mg/l of ethyl oxaloacetate, 0.1–1 mg/l of spermidine, 5–50 mg/l of Tween 80, purine and pyrimidine nucleosides in a ratio of the first to the second of between 1.5 and 2.2 the purine nucleosides consisting of adenosine and guanosine, in a ratio of the first to the second of between approximately 0.8 and 1.2, the pyrimidine nucleosides consisting of cytidine and uridine, in a ratio of the first to the second of between 1 and 3, 100–10,000 mg/l of glucose, 100–10,000 mg/l of malic acid, 0.020–0.583 mg/l of iron, 49.3–493 mg/l of potassium, 1.2–12 mg/l of magnesium, 2.7–27.2 mg/l of calcium, 1.18–3.15 g/l of sodium, 1,820–5,000 mg/l of chloride, 17.8–178.3 mg/l of phosphate ion, 33.6–336.0 mg/l of ammonium ion, 2,000–20,000 mg/l of an acidic buffer and 1,000–10,000 mg/l of a basic buffer.

2. Medium according to claim 1, characterized in that it contains 5–50 mg/l of adenosine, 3–30 mg/l of cytidine, 6–60 mg/l of guanosine, 1–10 mg/l of uridine, 0.2–5 mg/l of ferric pyrophosphate, 100–1,000 mg/l of dibasic potassium phosphate, 10–110 mg/l of magnesium chloride, 10–100 mg/l of calcium chloride, 100–1,000 mg/l of ammonium chloride, and 3,000–8,000 mg/l of sodium chloride.

3. Medium according to claim 1, characterized in that it contains at least one additional component selected from the group consisting of up to 0.022 mg/l of molybdenum, up to 0.010 mg/l of cobalt, up to 0.027 mg/l of manganese, up to 0.007 mg/l of zinc, up to 0.128 mg/l of copper, up to 0.088 mg/l of boron, up to 18.4 mg/l of sulfate ion, up to 0.1 mg/l of riboflavin, up to 0.005 mg/l of cyanocobalamin, up to 0.1 mg/l of menadione, up to 0.5 mg/l of boric acid and up to 5 mg/l of glycerol.

4. Medium according to claim 3, characterized in that it contains at least one component selected from the group consisting of up to 0.04 mg/l of ammonium molybdate, up to 0.04 mg/l of cobalt chloride, up to 0.1 mg/l of manganese chloride, up to 0.03 mg/l of zinc sulfate, up to 0.5 mg/l of copper sulfate and up to 100 mg/l of potassium sulfate.

5. Medium according to claim 1, characterized in that it contains 0.0005–0.005 mg/l of cyanocobalamin, 0.01–0.1 mg/l of menadione, 0.01–0.5 mg/l of mesoinositol, 0.01–0.1 mg/l of riboflavin, 0.1–5 mg/l of glycerol, 0.0004–0.04 mg/l of ammonium molybdate, 0.0004–0.04 mg/l of cobalt chloride, 0.001–0.1 mg/l of manganese chloride, 0.0003–0.03 mg/l of zinc sulfate, 2,000–20,000 mg/l of MOPS buffer, and 1,000–10,000 mg/l of Tris buffer.

6. Medium according to claim 1, characterized in that it contains at least 65 mg/l of alanine, 73 mg/l of arginine, 43 mg/l of asparagine, 53 mg/l of aspartic acid, 16 mg/l of cysteine, 37 mg/l of glutamine, 73 mg/l of glutamic acid, 66 mg/l of glycine, 22 mg/l of histidine, 54 mg/l of isoleucine, 84 mg/l of leucine, 89 mg/l of lysine, 33 mg/l of methionine, 44 mg/l of phenylalanine, 36 mg/l of proline, 320 mg/l of serine, 43 mg/l of threonine, 17 mg/l of tryptophan, 36 mg/l of tyrosine, 70 mg/l of valine, 0.03 mg/l of biotin, 0.03 mg/l of calcium pantothenate, 0.0008 mg/l of cyanocobalamin, 0.005 mg/l of folic acid, 0.05 mg/l of menadione, 0.15 mg/l of mesoinositol, 0.15 mg/l of nicotinamide, 0.15 mg/l of vitamin B6, 0.03 mg/l of riboflavin, 0.03 mg/l of thiamine chloride, 0.01 mg/l of lipoic acid, 1.5 mg/l of choline, 2.5 mg/l of glycerol, 5 mg/l of ethyl oxaloacetate, 0.75 mg/l of spermidine, 10 mg/l of Tween 80, 15 mg/l of adenosine, 10 mg/l of cytidine, 20 mg/l of guanosine, 6 mg/l of uridine, 750 mg/l of glucose, 500 mg/l of malic acid, 0.004 mg/l of ammonium molybdate, 0.004 mg/l of cobalt chloride, 0.016 mg/l of manganese chloride, 0.003 mg/l of zinc sulfate, 1.8 mg/l of ferric pyrophosphate, 0.25 mg/l of copper sulfate, 0.025 mg/l of boric acid, 50 mg/l of potassium sulfate, 230 mg/l of dibasic potassium phosphate, 100 mg/l of magnesium chloride, 90 mg/l of calcium chloride, 500 mg/l of ammonium chloride, 7,500 mg/l of sodium chloride, 15,000 mg/l of MOPS buffer, and 7,000 mg/l of Tris buffer.

7. Medium according to claim 1, characterized in that it additionally contains at least one peptide at a concentration of between 50 and 100 mg/l or a mixture of peptides at a concentration of between 50 and 1,000 mg/l, said peptides having a length of between 4 to 15 amino acids.

8. Medium according to claim 7, characterized in that the peptide is chosen from amongst the peptides having the following amino acid sequences:

SEQ ID NO: 1,

SEQ ID NO: 2, and

SEQ ID NO: 3.

9. Medium according to claim 1, characterized in that it contains in addition a beef extract.

10. Medium according to claim 1, characterized in that it contains a gelling agent at a concentration of approximately 10,000 mg/l.

11. Medium according to claim 9, characterized in that it contains between 2 and 10 g/l beef extract.

12. Medium according to claim 10, wherein said gelling agent comprises agarose.

13. A method for determining the activity of a substance on an infectious microorganism, comprising adding a substance and a first infectious microorganism to a first medium according to claim 1; and comparing the growth of said first infectious microorganism to the growth of a second infectious microorganism of a same type as said first infectious microorganism grown in a second medium of a same type as said first medium to which said substance has not been added.

* * * * *